US010113148B2

(12) United States Patent
Abe et al.

(10) Patent No.: US 10,113,148 B2
(45) Date of Patent: Oct. 30, 2018

(54) METHOD FOR OBTAINING MONOCYTES OR NK CELLS

(71) Applicants: Hiroyuki Abe, Tokyo (JP); Hiroaki Kawasaki, Tokyo (JP)

(72) Inventors: Hiroyuki Abe, Tokyo (JP); Hiroaki Kawasaki, Tokyo (JP)

(*) Notice: Subject to any disclaimer, the term of this patent is extended or adjusted under 35 U.S.C. 154(b) by 0 days.

(21) Appl. No.: 14/414,377

(22) PCT Filed: Jul. 10, 2013

(86) PCT No.: PCT/JP2013/068878
§ 371 (c)(1),
(2) Date: Jan. 12, 2015

(87) PCT Pub. No.: WO2014/021070
PCT Pub. Date: Feb. 6, 2014

(65) Prior Publication Data
US 2015/0197727 A1 Jul. 16, 2015

(30) Foreign Application Priority Data
Aug. 2, 2012 (JP) .................. 2012-172245

(51) Int. Cl.
*C12N 5/0783* (2010.01)
*C12N 5/0786* (2010.01)
*C07K 16/28* (2006.01)
*C12N 5/0784* (2010.01)
*A61K 39/00* (2006.01)

(52) U.S. Cl.
CPC ........ *C12N 5/0646* (2013.01); *C07K 16/2896* (2013.01); *C12N 5/0645* (2013.01); *A61K 2039/5158* (2013.01); *C12N 5/0639* (2013.01); *C12N 2500/90* (2013.01); *C12N 2501/02* (2013.01); *C12N 2501/22* (2013.01); *C12N 2501/2301* (2013.01); *C12N 2501/2302* (2013.01); *C12N 2501/2304* (2013.01); *C12N 2501/2306* (2013.01); *C12N 2501/2312* (2013.01); *C12N 2501/2315* (2013.01); *C12N 2501/25* (2013.01); *C12N 2501/26* (2013.01); *C12N 2501/58* (2013.01); *C12N 2501/599* (2013.01); *C12N 2506/115* (2013.01)

(58) Field of Classification Search
CPC . C12N 5/0646; C12N 5/0645; C07K 16/2896
USPC .............................. 435/347, 372; 530/388.73
See application file for complete search history.

(56) References Cited

U.S. PATENT DOCUMENTS

| 2010/0233192 | A1 | 9/2010 | Park et al. |
| 2012/0034251 | A1 | 2/2012 | Kumon et al. |
| 2014/0056945 | A1 | 2/2014 | Kumon et al. |

FOREIGN PATENT DOCUMENTS

| CN | 101603029 A | 12/2009 |
| CN | 102026647 | 4/2011 |
| EP | 2275114 | 1/2011 |
| JP | 2006-115826 | 5/2006 |
| JP | 2006-115826 | * 11/2006 |
| JP | 2007-297291 | 11/2007 |
| JP | 2010-259373 | 11/2010 |
| WO | 02/088328 | 11/2002 |
| WO | WO 02/088328 | * 11/2002 |
| WO | 20091119874 | 10/2009 |
| WO | 2009/151182 | 12/2009 |
| WO | 20111080740 | 7/2011 |

OTHER PUBLICATIONS

Aruga et al. (2004) Nendo Houkokusho (2004 Annual Report), Tokyo joshi ika daigaku sogo kenkyujo un'ei iinkai (Working Committee of Tokyo Women's Medical Univeristy Medical Research Institute), English translation, pp. 1-8.*
Cooper et al. (2004) Curr. Prot. Immunol., Supplement 60, Unit 7.34, published online May 1, 2004, pp. 1-12.*
Loza et al. (2004) Int. Immunol., vol. 16(1), 23-32.*
Ohkawa et al. (2001) Immunology, vol. 103, 281-290.*
Rydstrom et al. (2010) J. Leuk. Biol., vol. 87, 823-832.*
Arrighi et al. (1999) Blood, vol. 93(7), 2244-2252.*
ThermoFisher Scientific Product Description for AIM-V Medium, https://www.thermofisher.com/us/en/home/life-science/cell-culture/mammalian-cell-culture/specialty-media/t-cell-media/aim-v-medium.html, downloaded on Oct. 30, 2017.*
Liu, K., et al., "Development and homeostasis of dendritic cells," European Journal of Immunology, 2010, vol. 40, 2085-2130.
Aruga, Atsushi, et al., "New Development of Combined Cancer Immune Cell Therapy for Human Malignant Tumor," Bulletin 25 of Tokyo Women's Medical University Medical Research Institute, 2005, pp. 95-96 (2005).
Zamai, L, Ponti, C., Mirandola, P., Gobbi, G., Papa, S., Galeotti, L., . . . & Vitale, M. (2007). NK cells and cancer. The Journal of Immunology, 178(7), 4011-4016.
Castiello, L., Sabatino, M., Jin, P., Clayberger, C., Marincola, F. M., Krensky, A. M., & Stroncek, D. F. (2011). Monocyte-derived DC maturation strategies and related pathways: a transcriptional view. Cancer immunology, immunotherapy, 60(4), 457-466.
International Search Report for PCT/JP2013/068878, dated Aug. 27, 2013.
English translation of the International Preliminary Report on Patentability, International Patent Application No. PCT/JP2013/068878, dated Feb. 5, 2015.
European Search report of corresponding EP application no. 13825142.6, dated Dec. 9, 2015.
Fuss et al. "Isolation of Whole Mononuclear Cells from Peripheral Blood and Corde Blood" Curr Protoc Immunol. 2009; Chapter 7:Unit7.1.
Whiteside, T.L. "Isolation of human NK cells and generation of LAK activity" Curr Protoc Immunol. May 2001; Chapter 7:Unit 7.7, pp. 1-11.

(Continued)

*Primary Examiner* — Anne Marie S Wehbe
(74) *Attorney, Agent, or Firm* — Casimir Jones, SC; Robert A. Goetz

(57) ABSTRACT

The present invention relates to a method by which cells usable for an immune cell therapy are separated from peripheral blood and grown. The present invention makes it possible to provide immune system cells which are large enough in number to be used in the immune cell therapy.

3 Claims, 5 Drawing Sheets

(56) References Cited

OTHER PUBLICATIONS

Korthals et al. "Monocyte derived dendritic cells generated by IFN-alpha acquire mature dendritic and natural killer cell properties as shown by gene expression analysis." J Transl Med. Sep. 25, 2007; vol. 5, No. 1.
Carson et al. "Interleukin (IL) 15 is a novel cytokine that activates human natural killer cells via components of the IL-2 receptor." J Exp Med. Oct. 1, 1994;180(4):1395-403.
Niwa et al. "Enhancement of the antibody-dependent cellular cytotoxicity of low-fucose IgG1 Is independent of =FcgammaRIIIa functional polymorphism." Clin Cancer Res. Sep. 15, 2004;10(18 Pt 1):6248-55.
Arrighi et al. "Long-term culture of human CD34(+) progenitors with FLT3-ligand, thrombopoietin, and stem cell factor induces extensive amplification of a CD34(-31 )CD14(-31 ) and a CD34(-31)CD14(+) dendritic cell precursor." Blood. Apr. 1, 1999;93(7):2244-52.
Michaelis et al. "Glycyrrhizin inhibits highly pathogenic H5N1 influenza A virus-induced pro-inflammatory cytokine and chemokine expression in human macrophages." Medical Microbiology and Immunology, Nov. 2010, vol. 199, Issue 4, pp. 291-297.
Matsushita et al. "Separation methods of T cells, natural killer, and dendritic cells from peripheral blood of cancer patients using interleukin-2 and functional analysis of natural killer cells after separation." Immunopharmacol Immunotoxicol. 2007;29(1):31-47.
Office Action for KR patent application No. 10-2015-7000468, dated Sep. 27, 2016.
Office Action, CN Patent Application No. 201380034962.2 dated Aug. 4, 2016.
Office Action for CN Patent Application No. 201380034962.2, dated Mar. 2, 2017.
Office Action for CA Patent Application No. 2,876,260, dated Apr. 12, 2017, five pages.
Office Action for EP Patent Application No. 13825142.6, dated Apr. 19, 2017, six pages.
Braakman E et al: "IL-2- and IFN gamma-enhanced natural cytotoxic activity: analysis of the role of different lymphoid subsets and implications for activation routes.", Cellular Immunology May 1986, vol. 99, No. 2, May 1986 (May 1986), pp. 476-488, ISSN: 0008-8749.
Wang Liang-hua et al."Study of the Effect of Flt3L on the Immune Phenotypes of DCs", JMod Lab Med, Jul. 2004, vol. 19, No. 4.
Office Action, Corresponding CN Patent Application No. 201380034962.2, dated Nov. 24, 2015.
Office Action for related CN Application No. 201380034962.2, dated Mar. 15, 2018.
Office Action for related CA Application No. 2,876,260, dated Apr. 25, 2018.
EP Office Action, EP Patent Application No. 13825142.6, dated May 16, 2018.
Notification of Reexamination for CN Patent Application No. 201380034962.2, dated Jul. 18, 2018.

* cited by examiner

METHOD FOR OBTAINING MONOCYTES OR NK CELLS

CROSS-REFERENCE TO RELATED APPLICATIONS

The present application is a U.S. 371 National Stage Entry of pending International Patent Application No. PCT/JP2013/068878, international filing date Jul. 10, 2013, which claims priority to JP Patent Application No. 2012-172245, filed Aug. 2, 2012, the contents of which are incorporated by reference in their entireties.

TECHNICAL FIELD

The present invention relates to a method by which cells usable for an immune cell therapy are separated from peripheral blood and grown, more specifically to a method by which monocytes or NK cells are separated from peripheral blood and grown.

BACKGROUND ART

In recent years, many medical institutions offer an NK therapy and a monocyte-derived dendritic cell therapy, each of which is an immune cell therapy. A dendritic cell therapy which uses acquired immunity and an NK therapy which uses natural immunity are frequently applied as a combined therapy due to their advantages.

In the case of the combined therapy, dendritic cells and NK cells are obtained from independent blood so far. Components of monocytes to be differentiated into dendritic cells later are collected by apheresis (collection of blood components). Meanwhile, NK cells are collected from peripheral blood and grown. Therefore, the combined therapy generally requires two times of blood collection.

CITATION LIST

Non Patent Literatures

Non Patent Literature 1
Castiello et al., Cancer Immunol. Immunother., 60: 457-466, 2011.
Non Patent Literature 2
Zamai et al., J. Immunol., 178: 4011-4016, 2007.

SUMMARY OF INVENTION

Technical Problem

However, since even one of the above two types of blood collection (especially apheresis) imposes a burden on a patient, a physical burden on the patient further increases in a case where both the two types of blood collection are carried out. Accordingly, another method by which monocytes and NK cells are obtained and which imposes a lighter burden on a patient is required in an immune cell therapy.

In view of the problems, an object of the present invention is to provide immune system cells which are large enough in number to be used in an immune cell therapy while reducing a burden on a patient.

Solution to Problem

In order to attain the object, a method of the present invention for obtaining monocytes or NK cells, includes: (a) collecting a monocyte sample by separating the monocytes from peripheral blood by using an antibody specific for a surface marker of the monocytes; (b) collecting, as an NK cell sample, cell populations remaining after the separation of the monocytes; and (c) growing the monocytes or the NK cells by culturing the monocyte sample or the NK cell sample.

Advantages Effects of Invention

The present invention makes it possible to provide immune system cells which are large enough in number to be used in an immune cell therapy while reducing a burden on a patient.

DESCRIPTION OF EMBODIMENTS

Figure 1:
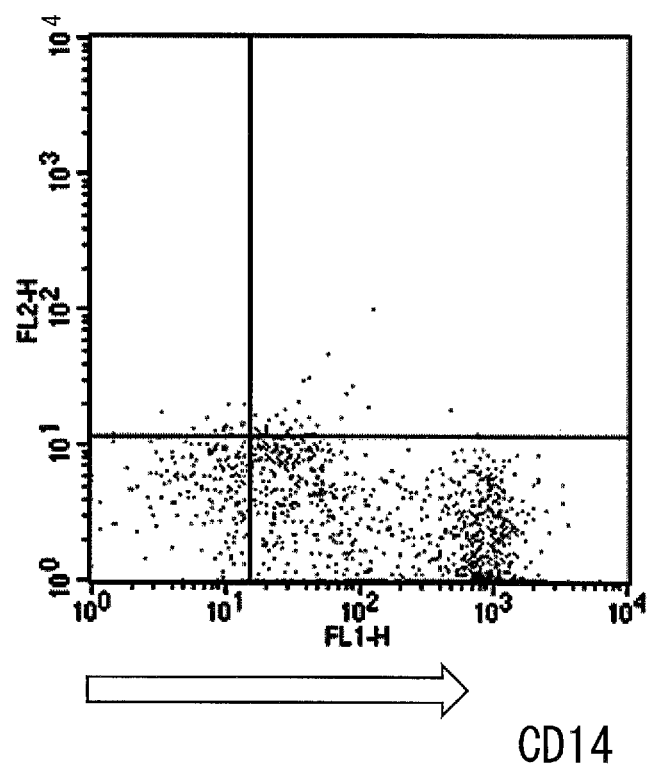
FIG. 1 shows a result of a FACS analysis which reveals that monocytes are selectively separated from peripheral blood.

A method of the present invention for obtaining monocytes or NK cells, includes: (a) collecting a monocyte sample by separating the monocytes from peripheral blood by using an antibody specific for a surface marker of the monocytes; (b) collecting, as an NK cell sample, cell populations remaining after the separation of the monocytes; and (c) growing the monocytes or the NK cells by culturing the monocyte sample or the NK cell sample.

That is, the method of the present invention includes the step of separating the monocytes and the NK cells from the peripheral blood assuming that at least one of the monocytes and the NK cells are grown later. This makes it unnecessary for the monocytes and the NK cells each obtained by the separation to be large enough in number to be used for performance of an immune cell therapy. According to the method of the present invention, by growing the monocytes and the NK cells each separated from a small amount of the peripheral blood, it is possible to provide immune system cells which are large enough in number to be used in the immune cell therapy.

A process carried out in the method of the present invention is specifically described below by taking, as an example, a case where necessary immune system cells are separated from a small amount of peripheral blood and then the immune system cells are grown until the immune system cells become large enough in number to be used in the immune cell therapy. Note that a term a "monocyte sample" herein refers to a sample including cell populations each made up mainly of the monocytes. Note also that a term an "NK cell sample" herein refers to a sample of cell populations each substantially including no monocytes but including the NK cells.

(Collection of Monocyte Sample and NK Cell Sample from Peripheral Blood)

As described earlier, the method of the present invention includes the step of separately collecting the monocyte sample and the NK cell sample from the peripheral blood. Further, as described earlier, this step is carried out through selective separation of the monocytes by using the antibody specific for the surface marker of the monocytes. Such an antibody is bonded to a carrier such as magnetic beads. The monocyte sample is obtained by mixing the carriers which are bonded to the antibody with a sample which includes the monocytes, and then collecting the carriers which are bonded via the antibody against the monocytes. Alternatively, the antibody can be labeled with biotin. According to this method, the monocytes can be separated by use of an interaction of streptavidin on the biotin with which the antibody is labeled.

Note here that the antibody is exemplified by an anti-CD14 antibody, an anti-CD16 antibody, and the like. The antibodies herein mentioned are merely taken as an example. Various antibodies which are specific for the surface marker of the monocytes which surface marker is publicly known to the present field can be used for the method of the present invention.

A method for selectively separating the monocytes by use of the antibody and the carriers as described earlier is exemplified by a method in which a RoboSep device (provided by Stem Cell Technologies) and a RoboSep Human CD14 Positive kit (provided by Stem Cell Technologies), a RoboSep negative Human monocyte kit (provided by Stem Cell Technologies), or the like are combined. The method, which makes it possible to separate the monocytes from a blood sample substantially not manually but automatically, is suitable for the method of the present invention. Stem Cell Technologies provides not only the kits (mentioned above) but also a kit such that a user selects an antibody to be used and combines the selected antibody with a reagent. Therefore, a combination of such a kit and the antibodies taken as an example makes it possible to separate the monocytes from the blood sample by use of the RoboSep device.

Note that a combination of the RoboSep device and the RoboSep negative Human NK cell kit, the RoboSep Human CD56 Positive kit, or the like makes it possible to separate the NK cells from the blood sample.

The peripheral blood is preferably partially separated before the monocytes are selectively separated by use of the antibody. The peripheral blood is preferably separated in advance by density gradient centrifugation by use of a Ficoll solution for separating mononuclear cell fractions. Since such density gradient centrifugation by use of the Ficoll solution is a general method for obtaining the NK cells for use in the immune cell therapy, no specific description thereof is particularly given here.

Note that the density gradient centrifugation is a general method whose object is to obtain activated T lymphocytes and NK cells each obtained by culturing, together with a suitable antibody and cytokine, the mononuclear cell fractions which have been separated. That is, unlike the method of the present invention, normally, the density gradient centrifugation is not carried out before the monocytes are separated and grown.

According to the method of the present invention, it is preferable to determine how many monocytes are included in the monocyte sample obtained as described earlier. It is possible to know in advance the number of days for which the monocytes included in the obtained monocyte sample need to be cultured so as to be grown to a desired number of monocytes, and if necessary, the number of days from the start of the culture to a day on which the monocytes are differentiated into dendritic cells. It can be determined, by a publicly-known flow cytometer and a FACS analysis in which a fluorescence-labeled anti-CD14 antibody is used, how many monocytes are included in the monocyte sample. An antibody to be used only needs to be an antibody specific for the surface marker of the monocytes. Therefore, for example, the antibodies for separating the monocytes (described earlier) can be used in the FACS analysis after being fluorescence-labeled.

As described later, according to the method of the present invention, the monocytes and the NK cells are selectively and independently grown by culturing the obtained monocyte sample and the obtained NK cell sample. Accordingly, the obtained monocyte sample and the obtained NK cell sample only need to include a desired number of cells (monocytes and NK cells, respectively) which are much smaller in number than cells whose number is required for the immune cell therapy. Therefore, the method of the present invention requires only a slight amount (e.g., 25 mL) of the peripheral blood. That is, the method of the present invention prevents blood collection in a large amount (e.g., several hundred mL to several L), which has been generally carried out in separation of the monocytes, from being carried out. Therefore, the method of the present invention allows a considerable reduction in temporal and physical burden due to blood collection in the immune cell therapy.

The peripheral blood in a small amount herein refers to peripheral blood in, for example, an amount of not more than 100 mL, preferably of not more than 75 mL, more preferably of not more than 50 mL, and most preferably of not more than 25 mL. Collection of blood in a smaller amount imposes a lighter burden on an individual. However, the number of monocytes and NK cells each contained in the peripheral blood greatly varies depending on a physical state of the individual. Therefore, an amount of the peripheral blood to be collected can be appropriately changed in accordance with a state of the individual to be subjected to blood collection and the required number of cells.

The peripheral blood from which the monocyte and the NK cells are separated can be peripheral blood collected a single time or a mixture of peripheral blood collected a plurality of times. Since the peripheral blood in a small amount is required (described earlier), the peripheral blood is normally collected a single time according to the method of the present invention.

(Growth of Monocytes)

According to the method of the present invention, the monocytes included in the collected monocyte sample are preferably selectively grown. According to the method of the present invention, the monocyte sample is cultured by use of a monocyte growth medium supplemented with Flt-3L which is known as a stem cell growth factor. As shown in Examples (described later), use of the monocyte growth medium allows growth of the monocytes which has not been generally carried out.

The monocyte growth medium uses, as a basic medium, a publicly-known medium for use in maintenance of the monocytes. The basic medium is commercialized by TAKARA BIO INC. as shown in Examples, is a medium obtained by partially modifying a commercially-available product, or has a composition similar to that of a commercially-available product. The monocyte growth medium can contain publicly-known cytokine (e.g., GM-CSF) for use in stimulation (promotion of growth, activation, and differentiation) of the monocytes. Furthermore, the monocyte growth medium can be supplemented with a suitable publicly-known antibiotic. Moreover, the monocyte growth medium can further contain plasma (self-plasma) separated from the peripheral blood from which the monocyte sample has been collected. Other suitable additives to the monocyte growth medium, which are various additives for use in maintenance of the monocytes and differentiation into the dendritic cells, are publicly known to a person skilled in the art.

Flt-3L is contained in the monocyte growth medium in, for example, a concentration of 500 IU/mL to 5000 IU/mL, more preferably of 1000 IU/mL to 4000 IU/mL, and most preferably of 2000 IU/mL. GM-CSF is contained in the monocyte growth medium in, for example, a concentration of 500 IU/mL to 5000 IU/mL, more preferably of 1000 IU/mL to 2500 IU/mL, and most preferably of 1000 IU/mL.

The monocyte sample is cultured by use of the monocyte growth medium for any period (until a desired number of monocytes are obtained). Such a period is changed in accordance with the number of monocytes included in the obtained monocyte sample. If the case of Examples (described later) is taken as an example, the period is approximately 14 days in a case where the monocyte sample is collected from 25 mL of the peripheral blood. In this case, the monocytes of the monocyte sample can be grown to, for example, approximately $1\times10^7$ cells by the culture for approximately 14 days.

As is clear from the above description, Flt-3L of the present invention is an additive to be added to the monocyte growth medium (e.g., a promoter of growth of the monocytes). Further, the present invention relates to use of Flt-3L as an additive to be added to the monocyte growth medium.

As described later, according to the method of the present invention, a factor for differentiation of the monocytes into the dendritic cells can be added to cultures during the culture (e.g., on the third day of the culture). That is, it is not always necessary to grow only the monocytes to, for example, approximately $1\times10^7$ cells. Accordingly, in this case, only the monocytes are selectively cultured for approximately three days, and the entire period of the culture is approximately 14 days. Monocyte-derived dendritic cells are actually used in the immune cell therapy. Therefore, according to the method of the present invention, it is preferable to differentiate the monocytes into the dendritic cells for actual use while growing the monocytes. The following section discusses how to differentiate the monocytes into the dendritic cells while growing the monocytes.

(Differentiation of Monocytes into Dendritic Cells)

According to the method of the present invention, the monocytes are differentiated into the dendritic cells by use of the monocyte growth medium further supplemented with, for example, cytokine. The cytokine with which the monocyte growth medium is supplemented in the differentiation of the monocytes into immature dendritic cells is generally IL-4 and GM-CSF. IL-4 and GM-CSF each of which can be used to differentiate the monocytes into the immature dendritic cells are commercially available or can be obtained by expressing (recombinant) human genes coding IL-4 or GM-CSF.

Then, the immature dendritic cells are pulsed by use of antigen-containing biological materials (e.g., a tumor cell (a tumor cell-containing tissue piece), a tumor marker, a piece of a focus of a specific disease, a virus-infected cell, and the like), or antigen-forming biological materials (e.g., antigenic peptide, protein (long-chain peptide) or a fragment thereof, antigenic nucleic acid, and the like). The pulsed immature dendritic cells are matured into mature dendritic cells by being cultured in the medium to which a physiologically active substance and an adjuvant have been further added.

The cytokine, the physiologically active substance, and the adjuvant for use in differentiation into the mature dendritic cells are, for example, IL-1β, IL-6, TNFα, PGE2, picibanil chloride (OK432), and the like, and these are available as commercial items or can be obtained by expressing (recombinant) human genes coding such cytokine as mentioned above. Note that a combination of the cytokine, the physiologically active substance, and the adjuvant which combination is the most suitable for differentiation of the immature dendritic cells into the mature dendritic cells is mentioned here. The combination which is essential for the differentiation is, for example, a combination of PGE2 and OK432.

IL-1β is contained in the monocyte growth medium for differentiation of the monocytes into the dendritic cells in, for example, a concentration of 2 ng/mL to 100 ng/mL, more preferably of 5 ng/mL to 50 ng/mL, and most preferably of 10 ng/mL. IL-6 is contained in the monocyte growth medium for differentiation of the monocytes into the dendritic cells in, for example, a concentration of 200 IU/mL to 6000 IU/mL, more preferably of 500 IU/mL to 4000 IU/mL, and most preferably of 1000 IU/mL. TNFα is contained in the monocyte growth medium for differentiation of the monocytes into the dendritic cells in, for example, a concentration of 2 ng/mL to 100 ng/mL, more preferably of 10 ng/mL to 50 ng/mL, and most preferably of 20 ng/mL. PGE2 is contained in the monocyte growth medium for differentiation of the monocytes into the dendritic cells in, for example, a concentration of 0.05 µg/mL to 5 µg/mL, more preferably of 0.5 µg/mL to 2 µg/mL, and most preferably of 1 µg/mL. Picibanil chloride is contained in the monocyte growth medium for differentiation of the monocytes into the dendritic cells in, for example, a concentration of 0.005 KE to 10 KE, more preferably of 0.05 KE to 5 KE, and most preferably of 0.1 KE.

According to the method of the present invention, in a case where the monocyte sample has been obtained from 25 mL of the peripheral blood, the monocyte sample is cultured for approximately 14 days (described earlier). In this case, the cytokine for differentiating the monocytes into the immature dendritic cells is added to the medium on, for example, the third day of the culture. The pulse is carried out on, for example, the eleventh day of the culture. The cytokine and the adjuvant each of which induces differentiation into the mature dendritic cells are added to the medium after the pulse. A desired number of dendritic cells (e.g., $1\times10^7$ cells) are obtained on the fourteenth day of the culture (see Example 2-1.).

As is clear from the above description, Flt-3L of the present invention is an additive to be added to the medium for obtaining the dendritic cells (e.g., a promoter of growth of the dendritic cells). Further, the present invention relates to use of Flt-3L as an additive to be added to the medium for obtaining the dendritic cells.

The above description has discussed the respective periods for growth and differentiation of the monocytes by taking, as an example, a case where the monocyte sample has been obtained from 25 µmL of the peripheral blood. However, the period for the culture can be extended or shortened in accordance with the number of monocytes included in the obtained monocyte sample (described earlier). Such setting of the period for the culture is a matter empirically known to a person skilled in the art.

The number of cells can be counted at any point in time by use of, for example, trypan blue. A ratio in which the monocytes are included in the counted cell populations can be determined by the FACS analysis in which the anti-CD14 antibody that is fluorescence-labeled is used, and a ratio in which the dendritic cells are included in the counted cell populations can be determined by the FACS analysis in which an anti-CD83 antibody that is fluorescence-labeled is used. Accordingly, the respective periods for the culture and the differentiation can be freely changed at respective points in time at which points the number of cells and cell types are determined.

The dendritic cells incorporate, into the cells, foreign matters in the body (e.g., viruses, bacteria, and fragments thereof). Then, the dendritic cells activate an immune response specific for the foreign matters by presenting an antigen (the foreign matters or the foreign matters which have been treated) to other immune system cells. Accordingly, in a case where the monocyte-derived dendritic cells are pulsed by use of a disease marker specific for a disease (e.g., a tumor) which is normally not recognized as a foreign matter by the dendritic cells (e.g., WT1 for a tumor), it is possible to obtain the dendritic cells which allow treatment of various diseases.

(Growth of NK Cells)

According to the method of the present invention, the NK cells included in the collected NK cell sample are preferably selectively grown. According to the method of the present invention, the NK cell sample is cultured by use of an NK cell growth medium supplemented with an anti-CD56 antibody which recognizes a surface marker of the NK cells. Use of the NK cell growth medium makes it possible to selectively grow the NK cells included in the NK cell sample (the cell populations remaining after separation of the monocytes) (see Examples described later).

Generally, the NK cells for use in the immune cell therapy are grown by culturing peripheral blood-derived mononuclear cell fractions by use of a medium containing cytokine (IL-2, IL-12, and IL-15) which induces differentiation, maturation, activation, and growth of the NK cells. However, when the NK cell sample of the present invention was cultured by use of such a medium, the number of the NK cells grown was insufficient (see Example 2-6.). Accordingly, neither a conventionally-known condition for growing the NK cells nor a conventionally-known method for growing the NK cells is applicable to the method of the present invention.

The NK cell growth medium uses, as a basic medium, a publicly-known medium for use in growth of the NK cells. The basic medium is commercialized by Kohjin Bio Co., Ltd. as shown in Examples, is a medium obtained by partially modifying a commercially-available product, or has a composition similar to that of a commercially-available product. The NK cell growth medium can contain IL-2, IL-12, and IL-15 for use in normal growth and activation of the NK cells. An additive to the NK cell growth medium other than the additives mentioned above is publicly known to a person skilled in the art through the conventionally-known condition for growing the NK cells (described earlier) and the conventionally-known method for growing the NK cells (described earlier).

The anti-CD56 antibody is contained in the NK growth medium for growth and activation of the NK cells in, for example, a concentration of 1 μg/mL to 200 μg/mL, more preferably of 10 μg/mL to 150 μg/mL, and most preferably of 80 μg/mL. Note that it is possible to use, as the anti-CD56 antibody, which is directly added to the medium according to the above description, an anti-CD56 antibody which is fixed to any support (e.g., a plastic flask and a dish) (a coated anti-CD56 antibody). In a case where the anti-CD56 antibody is coated, the above range of the concentration indicates a used amount of the anti-CD56 antibody with respect to a used amount of the medium. IL-2 is contained in the NK growth medium for growth and activation of the NK cells in, for example, a concentration of 100 IU/mL to 3000 IU/mL, more preferably of 1000 IU/mL to 2000 IU/mL, and most preferably of 1750 IU/mL. IL-12 is contained in the NK growth medium for growth and activation of the NK cells in, for example, a concentration of 100 IU/mL to 5000 IU/mL, more preferably of 500 IU/mL to 3000 IU/mL, and most preferably of 2000 IU/mL. IL-15 is contained in the NK growth medium for growth and activation of the NK cells in, for example, a concentration of 100 IU/mL to 5000 IU/mL, more preferably of 500 IU/mL to 3000 IU/mL, and most preferably of 2000 IU/mL.

The NK cell sample can be cultured for a period similar to the period for which the monocyte sample (described earlier) is cultured. For example, the NK cell sample of the present invention is cultured for approximately 14 days by use of the NK cell growth medium. The NK cells can be grown to, for example, approximately $1 \times 10^9$ cells by the culture for approximately 14 days (see Example 2-3.).

As is clear from the above description, the anti-CD56 antibody of the present invention is an additive to be added to the NK cell growth medium (e.g., a promoter of growth of the NK cells). Further, the present invention relates to use of the anti-CD56 antibody as an additive to be added to the NK cell growth medium.

The number of cells included in the cultures is counted at any point in time during the culture by use of trypan blue as in the case of the monocytes. In this case, a ratio in which the NK cells are included in the cell populations of the cultures can be determined by the FACS analysis in which the anti-CD56 antibody that is fluorescence-labeled is used.

A main role which is normally played by the NK cells is an attack on tumor cells and infected cells. Accordingly, the NK cells which have been activated are usable for treatment of cancer and infectious diseases. Therefore, in a case where together with the NK cells, the dendritic cells which are matured by a pulse by use of a tumor marker are used, a therapeutic effect especially excellent for treatment of cancer can be expected.

As described earlier, the method of the present invention makes it possible to obtain, from a small amount of the peripheral blood, the NK cells which are large enough in number to be used in the immune cell therapy and the dendritic cells which are large enough in number to be used in the immune cell therapy. Accordingly, the method of the present invention allows a considerable reduction in temporal and physical burden on a patient due to blood collection. In particular, there are many cases where immune cells need to be administered a plurality of times for a long period of time in treatment of cancer by the immune cell therapy. Such a case not only causes blood collection in a large amount to impose an enormous burden on a patient but also forces treatment itself to be postponed or suspended since blood collection cannot be carried out with respect to a patient depending on a state of the patient. The method of the present invention thus easily makes it possible to continuously carry out the immune cell therapy while reducing a burden on a patient.

The method of the present invention is a method for separating and growing useful immune system cells contained in blood collected from an individual (e.g., a human). The monocytes obtained in accordance with the present invention are materials for preparing the dendritic cells for use in the immune cell therapy by being differentiated. Further, the NK cells and the dendritic cells each obtained in accordance with the present invention are cells (pharmaceuticals) which are directly used in the immune cell therapy.

[Conclusion]

A method of the present invention for obtaining monocytes or NK cells, includes: (a) collecting a monocyte sample by separating the monocytes from peripheral blood by using an antibody specific for a surface marker of the monocytes; (b) collecting, as an NK cell sample, cell populations remaining after the separation of the monocytes; and (c) growing the monocytes or the NK cells by culturing the monocyte sample or the NK cell sample.

The method of the present invention is preferably configured such that in the step (c), the monocytes are grown by culturing the monocyte sample by use of a first medium containing Flt-3L.

The method of the present invention is preferably configured to further include: (d) differentiating the monocytes into dendritic cells while growing the monocytes by adding GM-CSF and IL-4 to the first medium.

The method of the present invention is preferably configured such that in the step (c), the NK cells are grown by culturing the NK cell sample by use of a second medium containing an anti-CD56 antibody or IFN-γ.

The method of the present invention is preferably configured such that in the step (c), the NK cells are further grown by culturing the NK cell sample by use of a second medium containing an anti-CD56 antibody or IFN-γ.

The method of the present invention is preferably configured such that the second medium contains the anti-CD56 antibody.

The method of the present invention is preferably configured such that the second medium further contains IL-2, IL-12, and IL-15.

The method of the present invention is preferably configured such that the peripheral blood is collected a single time from an individual.

EXAMPLES

[1. Separation of Monocytes and NK Cells From Peripheral Blood Collected Single Time]

(1-1. Selective Separation of Monocytes and Confirmation Thereof)

By density gradient centrifugation (30 minutes, 900 g, 20° C.) by use of a Ficoll solution (GE Healthcare), monocyte fractions were separated from 25 mL of peripheral blood collected from a healthy person. Monocytes were further separated from the obtained monocyte fractions by use of the RoboSep device (Stem Cell Technologies). In the separation of the monocytes from the monocyte fractions, the RoboSep Human CD14 Positive kit (Stem Cell Technologies) was used as a reagent for selectively separating the monocytes. A procedure through which the monocytes were selectively separated and all the other necessary reagents for use in the selective separation of the monocytes were in conformity with (i) an operation program of the RoboSep device which operation program was compatible with the reagents and (ii) a user manual attached to the RoboSep device.

A part of a sample obtained in accordance with the above operation was mixed with the fluorescence-labeled anti-CD14 antibody (BioLegend, antibody against a cell surface marker of the monocytes). Then, it was examined by use of a BD FACSCalibur (Registered Trademark) flow cytometer (Nippon Becton Dickinson Company, Ltd.) how many monocytes were contained in the resulting mixture. FIG. 1 shows a result of the FACS analysis. FIG. 1 shows a histogram of a quadrant region which histogram was obtained by carrying out the FACS analysis on CD14 positive cells. As shown in FIG. 1, it was confirmed that the monocytes each having a surface on which CD14 was expressed were mainly included in the sample.

(1-2. Confirmation of Presence of NK Cells)

Figure 2:
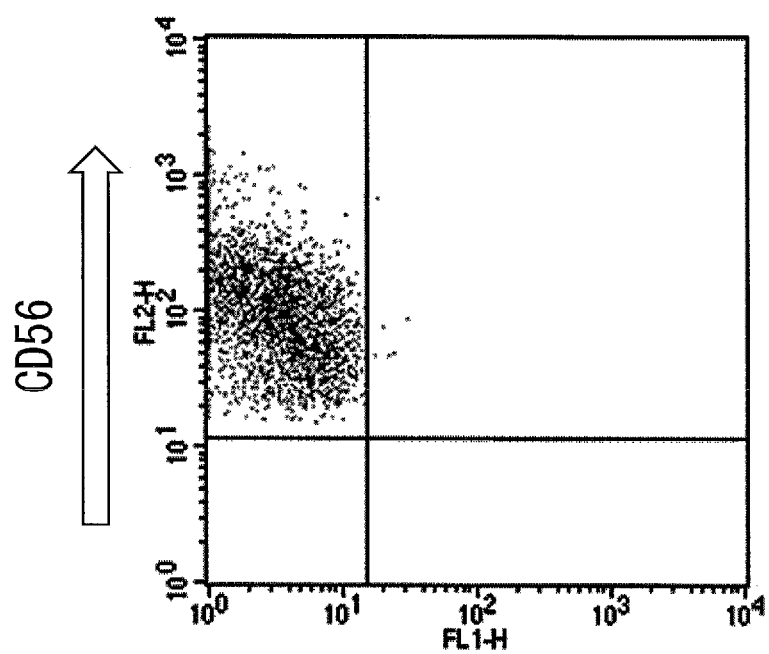
FIG. 2 shows a result of the FACS analysis which reveals that a sample remaining after the selective separation of the monocytes include NK cells.

A part of the remaining cell populations of the monocytes obtained in 1-1. were mixed with the fluorescence-labeled anti-CD56 antibody (BioLegend, antibody against a cell surface marker of the NK cells). Then, it was examined by use of the BD FACSCalibur (Registered Trademark) flow cytometer how many NK cells were contained in the resulting mixture. FIG. 2 shows a result of the FACS analysis. FIG. 2 shows a histogram of a quadrant region which histogram was obtained by carrying out the FACS analysis on CD56 positive cells. As shown in FIG. 2, it was revealed that useful NK cells were included in the cell populations which have been conventionally disposed of.

As described earlier, it was revealed that by not only conventionally separating only the monocytes but also further collecting the cell populations which have been disposed of so far, the monocytes and the NK cells were made available separately from a small amount of the peripheral blood obtained by single blood collection.

[2. Growth of Monocytes and NK Cells]

(2-1. Growth of Monocytes and Differentiation Into Dendritic Cells in Accordance with the Present Invention)

Figure 3:
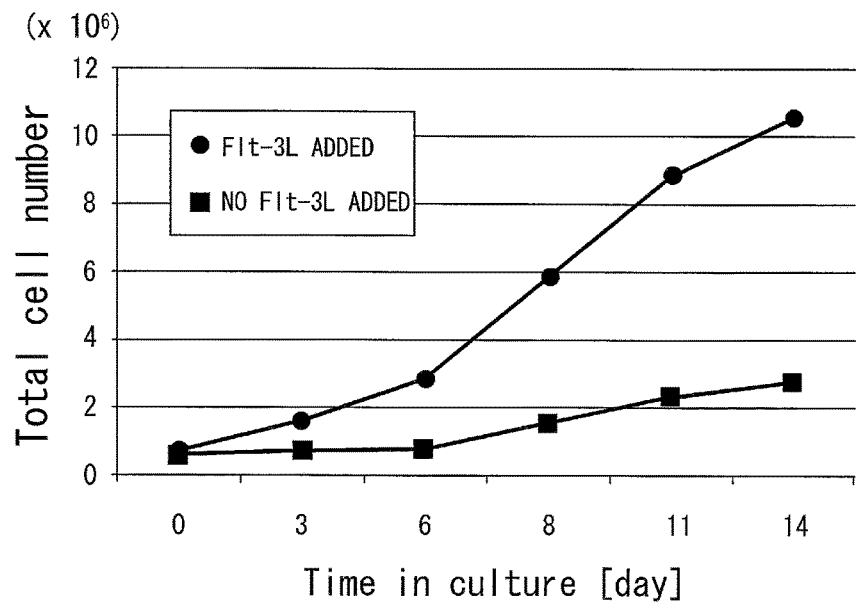
FIG. 3 shows a change over time in number of cells of (i) monocytes grown in accordance with a culture method of the present invention and a conventional culture method and (ii) dendritic cells differentiated from the monocytes.

The monocytes separated in 1-1. were grown and then differentiated into the dendritic cells. The monocytes were selectively grown until the third day from the zeroth day of culture by use of a medium A1 obtained by supplementing an X-VIVO-15 medium (TAKARA BIO INC.) with 1000 IU/mL of GM-CSF (Miltenyi Biotec), 2000 IU/mL of Flt-3L (Cellgenix), 50 ng/mL of gentamicin, and 5% of self-plasma. On the third day, 1000 IU/mL of IL-4 (Miltenyi Biotec) was added to the medium A1 (a medium A2). Then, the monocytes were differentiated into immature dendritic cells by continuing the culture until the eleventh day. On the eleventh day, the immature dendritic cells were pulsed by use of MUC1 peptide (Thermo Fisher), WT1 encapsulated in a lipid vesicle, or the like. Subsequently, the immature dendritic cells were differentiated into mature dendritic cells by use of a medium A3 obtained by adding, to the medium A2, 10 ng/mL of IL-1β (Miltenyi Biotec), 1000 IU/mL of IL-6 (Miltenyi Biotec), 1 µg/mL of PGE2 (Cayman Chemical Company), 20 ng/mL of TNF-α (Miltenyi Biotec), and 0.1 KE of picibanil chloride (CHUGAI PHARMACEUTICAL CO., LTD.). All the above culture was carried out at 37° C. in the presence of 5% $CO_2$. The number of cells (number of cells/mL) obtained on each of the zeroth, third, sixth, eighth, eleventh, and fourteenth days of the culture was determined by trypan blue dyeing. FIG. 3 shows a change over time in determined number of cells.

As shown in FIG. 3 (Flt-3L ADDED), it was confirmed that $7.4 \times 10^5$ cells obtained on the zeroth day of the culture were grown to $1.05 \times 10^7$ cells on the fourteenth day of the culture. According to the above description, the dendritic cells differentiated from the monocytes and grown were $1.05 \times 10^7$ cells. This made it possible to obtain, from 25 mL of peripheral blood collected a single time, the dendritic cells which are large enough in number to be used in the immune cell therapy.

(2-2. Examination of Grown Cell Types)

Figure 5:
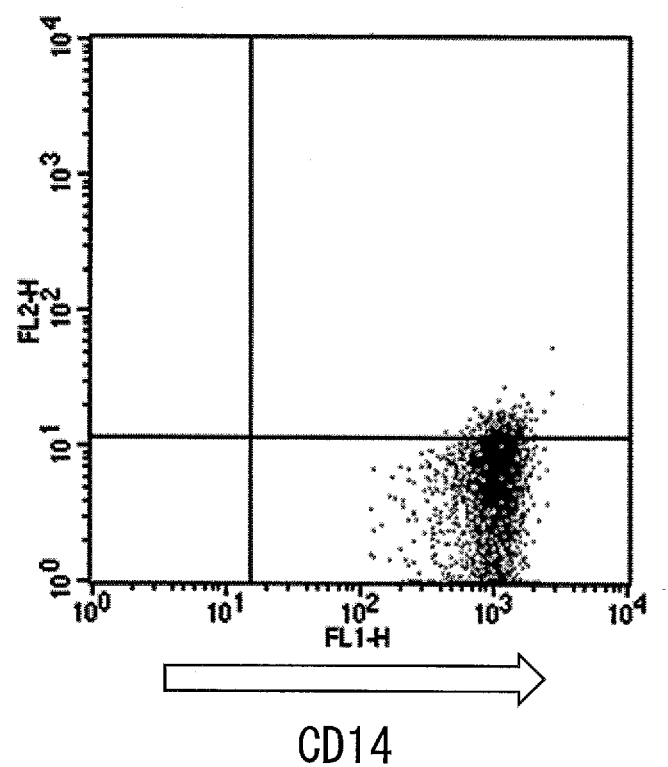
FIG. 5 shows a result of the FACS analysis which reveals that the monocytes are grown (on the third day).
Figure 6:
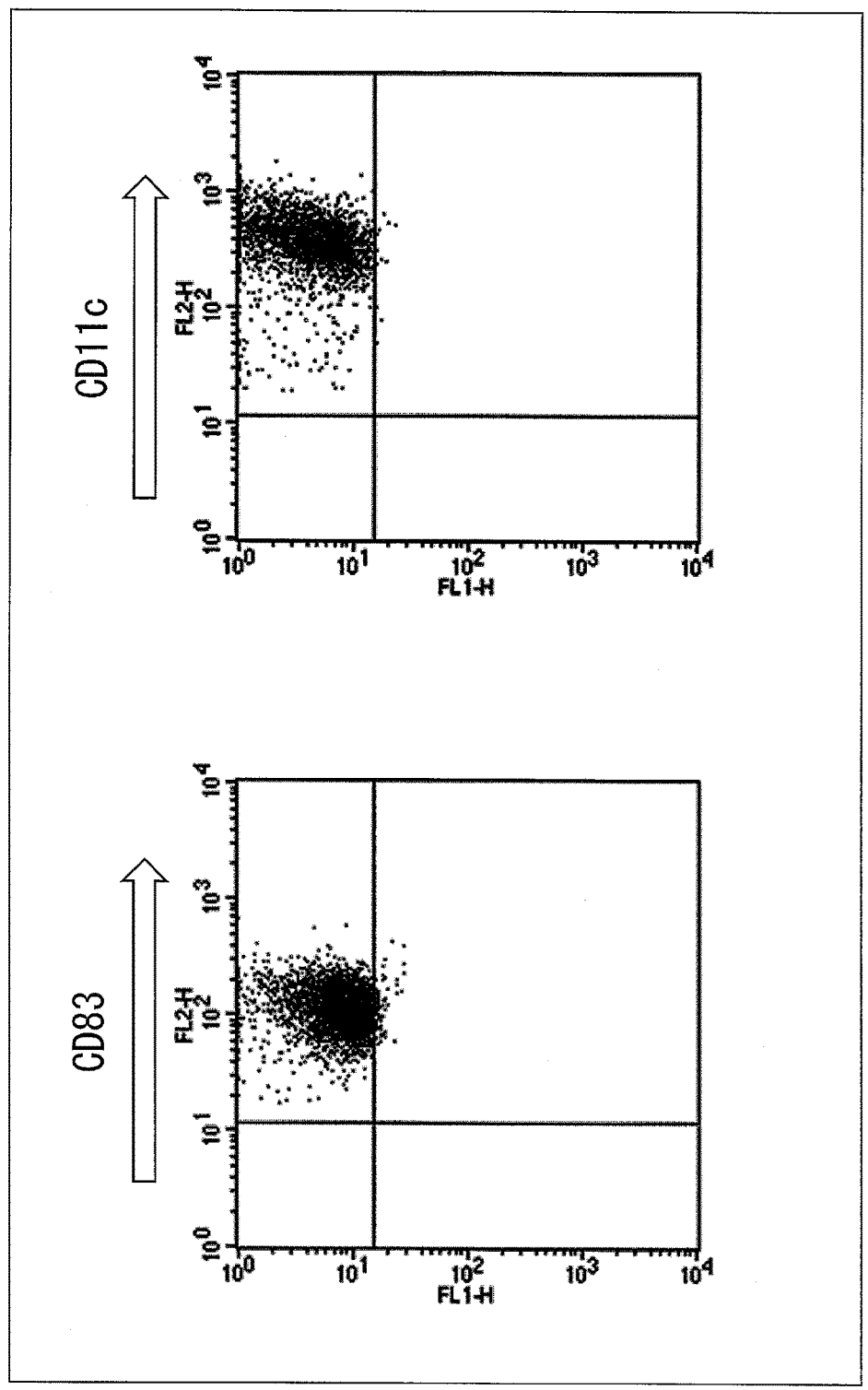
FIG. 6 shows a result of the FACS analysis which reveals that the dendritic cells are grown.

Types of grown cells were examined by the FACS analysis on each of the third and fourteenth days of the culture in 2-1. A part of the cultures obtained on the third day were examined by use of the fluorescence-labeled CD14 antibody (BioLegend). A part of the cultures obtained on the fourteenth day were examined by use of a fluorescence-labeled anti-CD11c antibody (Becton, Dickinson and Company) and the fluorescence-labeled anti-CD83 antibody (eBioscience). All the FACS analysis was carried out by use of the BD FACSCalibur (Registered Trademark) flow cytometer (Nippon Becton Dickinson Company, Ltd.). FIGS. 5 and 6 each show a result of the FACS analysis.

As shown in FIG. 5, it was revealed that the cultures obtained on the third day included substantially only the monocytes. As shown in FIG. 6, it was revealed that the cultures obtained on the fourteenth day included substantially only the mature dendritic cells. Therefore, it was confirmed that the growth and the differentiation proceeded as desired in 2-1.

(2-3. Culture of Monocytes by Use of Publicly-Known Factor for Stimulating Monocytes)

The monocytes were separated by carrying out again the operation of 1-1. besides the operation of 2-1. These monocytes were cultured as in the case of those in 2-1. except that no Flt-3L was added to the medium. FIG. 3 shows the number of cells obtained at each point in time of this culture. As shown in FIG. 3 (NO Flt-3L ADDED), according to such a general method for inducing differentiation of the monocytes, the cells were merely grown to $2.8 \times 10^6$/mL on the fourteenth day of the culture.

As described earlier, according to the method of the present invention, by using a factor whose action of growing the monocytes had not been known, it was possible to obtain the mature dendritic cells which were large enough in number to be used for medical purposes.

(2-4. Selective Growth of NK Cells)

Figure 4:
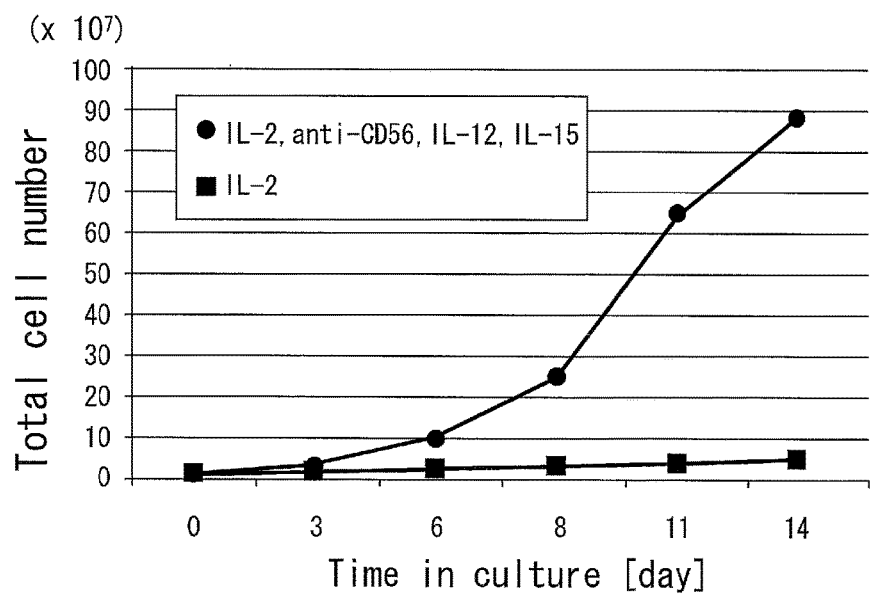
FIG. 4 shows a change over time in number of cells of NK cells grown in accordance with the culture method of the present invention and the conventional culture method.

The cell populations obtained in 1-1. were cultured as below. On the zeroth day of the culture, lymphocytes were activated at 38° C. in the presence of 5% $CO_2$ for 24 hours by use of a medium obtained by supplementing KBM502 Medium (Kohjin Bio Co., Ltd.) (containing 1750 IU/mL of IL-2 in advance) with 200 IU/mL of IL-12 (Miltenyi Biotec), 2000 IU/mL of IL-15 (Cellgenix), 80 µg/mL of the anti-CD56 antibody (BioLegend), and 5% of self-plasma. Then, the cells were cultured until the fourteenth day by changing a condition for the culture so that the cells were cultured at 37° C. in the presence of 5% $CO_2$. The number of cells (number of cells/mL) obtained on each of the zeroth, third, sixth, eighth, eleventh, and fourteenth days of the culture was determined by trypan blue dyeing. FIG. 4 shows a change over time in determined number of cells.

As shown in FIG. 4 (IL-2, anti-CD56, IL-12, IL-15), it was confirmed that $9.6 \times 10^6$ cells obtained on the zeroth day of the culture were increased to $8.8 \times 10^8$ cells on the fourteenth day of the culture. According to the above description, the grown NK cells were approximately $10^9$ cells. This made it possible to obtain, from 25 mL of the peripheral blood collected a single time, the NK cells which are large enough in number to be used in the immune cell therapy.

(2-5. Examination of Grown Cell Types)

Figure 7:
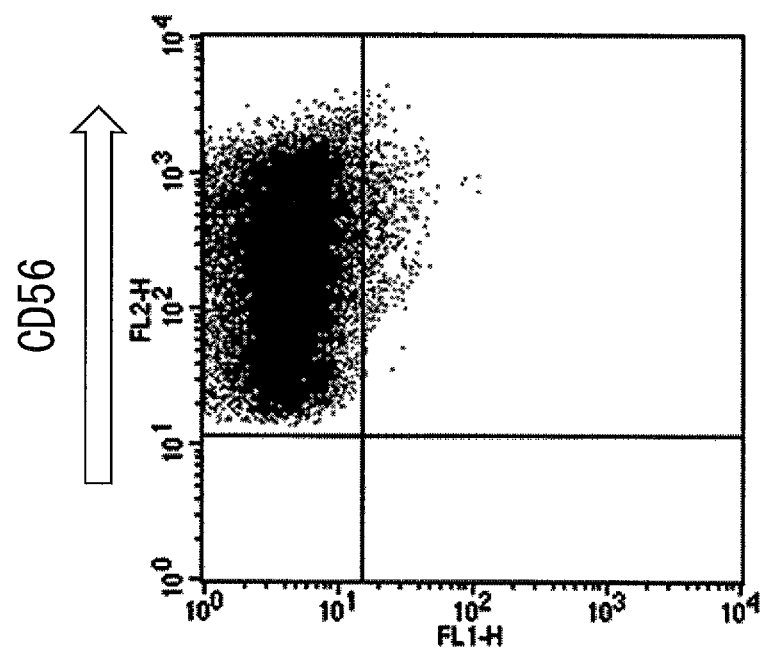
FIG. 7 shows a result of the FACS analysis which reveals that the NK cells are grown.

Types of grown cells were examined by the FACS analysis on the fourteenth day of the culture in 2-4. A part of the cultures were examined by use of the fluorescence-labeled anti-CD56 antibody (BioLegend). The FACS analysis was carried out by use of the BD FACSCalibur (Registered Trademark) flow cytometer (Nippon Becton Dickinson Company, Ltd.). FIG. 7 shows a result of the FACS analysis.

As shown in FIG. 7, it was confirmed that the cultures including substantially only the NK cells were finally obtained.

(2-6. Growth of NK Cells by Using Only IL-2 as Growth Factor)

The cell populations including the NK cells were obtained by carrying out again the operation of 1-1. besides the operation of 2-4. These cell populations were cultured as in the case of those in 2-4. except that only IL-2 was used as a growth factor. FIG. 4 shows the number of cells obtained at each point in time of this culture. As shown in FIG. 4 (IL-2), according to such a method, the cells were merely increased to $4.6 \times 10^7$ cells on the fourteenth day of the culture. This makes it impossible to obtain sufficient cells.

The above description revealed that IL-2 was insufficient and at least one of IL-12, IL-15, and the anti-CD56 antibody was necessary for obtaining a desired number of NK cells by selectively growing the NK cells separated from the peripheral blood.

As is clear from Examples, it was possible to obtain, from a slight amount of 25 mL of the peripheral blood collected a single time, the NK cells which are large enough in number to be used in the immune cell therapy and the dendritic cells which are large enough in number to be used in the immune cell therapy. This makes it possible to obtain two types of useful immune system cells in large amounts from the peripheral blood in an amount sufficient enough for use in examination. That is, the method of the present invention allows an increase in usefulness of the immune cell therapy in which the dendritic cells and the NK cells are used (allows a significant reduction in temporal and physical burden on a subject to blood collection).

The present invention is not limited to the description of the embodiments and examples above, but may be altered by a skilled person within the scope of the claims. An embodiment based on a proper combination of technical means disclosed in different embodiments is encompassed in the technical scope of the present invention.

INDUSTRIAL APPLICABILITY

The present invention is usable for an immune cell therapy for various diseases.

The invention claimed is:
1. A method for obtaining monocytes or NK cells, comprising:
   (a) collecting a monocyte sample by separating the monocytes from peripheral blood by using an antibody specific for a surface marker of the monocytes, wherein the peripheral blood is obtained from a human;
   (b) collecting, as an NK cell sample, cell populations remaining after the separation of the monocytes; and
   (c) growing the monocytes or the NK cells by culturing at least one of the monocyte sample and the NK cell sample,
   wherein in the step (c), at least the NK cells are grown by culturing the NK cell sample without carrying out further separation steps by use of a second medium containing an anti-CD56 antibody.
2. The method as set forth in claim 1, wherein the second medium further contains IL-2, IL-12, and IL-15.

3. The method as set forth in claim 1, wherein in the step (c), the monocytes are further grown by culturing the monocyte sample by use of a first medium containing Flt-3L.

\* \* \* \* \*